(12) United States Patent
Chen et al.

(10) Patent No.: US 10,775,361 B2
(45) Date of Patent: Sep. 15, 2020

(54) MONITORING CONTROL CHANNEL WITH DIFFERENT ENCODING SCHEMES

(71) Applicant: QUALCOMM Incorporated, San Diego, CA (US)

(72) Inventors: Wanshi Chen, San Diego, CA (US); Hao Xu, San Diego, CA (US); Tingfang Ji, San Diego, CA (US); Jing Jiang, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 566 days.

(21) Appl. No.: 15/389,282

(22) Filed: Dec. 22, 2016

(65) Prior Publication Data

US 2018/0026740 A1 Jan. 25, 2018

Related U.S. Application Data

(60) Provisional application No. 62/365,818, filed on Jul. 22, 2016.

(51) Int. Cl.
*H04L 1/18* (2006.01)
*G01N 33/487* (2006.01)
(Continued)

(52) U.S. Cl.
CPC ......... *G01N 33/487* (2013.01); *G06F 16/283* (2019.01); *H01J 49/005* (2013.01);
(Continued)

(58) Field of Classification Search
CPC ..... H04L 1/0099; H04L 5/001; H04L 5/0053; H04W 8/22
See application file for complete search history.

(56) References Cited

U.S. PATENT DOCUMENTS

2010/0023830 A1* 1/2010 Wengerter ............ H04L 1/0025
714/748
2010/0227569 A1* 9/2010 Bala ...................... H04L 5/0007
455/73

(Continued)

FOREIGN PATENT DOCUMENTS

EP 0950301 A1 10/1999
EP 2945446 A1 11/2015

OTHER PUBLICATIONS

CATR: "Considerations on Channel Coding for NR", 3GPP Draft; R1-163130, 3rd Generation Partnership Project (3GPP), Mobile Competence Centre ; 650, Route De Lucioles; F-06921 Sophia-Antipolis Cedex; France, vol. RAN WG1, No. Busan, Korea; Apr. 11, 2016-Apr. 15, 2015, Apr. 1, 2016 (Apr. 1, 2016), XP051079772, Retrieved from the Internet: URL: http://www.3gpp.org/ftp/tsg_ran/WG1_RL1/TSGR1_84b/Docs/ [retrieved on Apr. 1, 2016], pp. 1-3.

(Continued)

*Primary Examiner* — Brandon M Renner
(74) *Attorney, Agent, or Firm* — Patterson + Sheridan, LLP

(57) ABSTRACT

Certain aspects of the present disclosure are generally directed to monitoring different decoding candidates assuming different encoding schemes. For example, certain aspects of the present disclosure are directed to a method for wireless communication. The method generally includes determining a first encoding scheme used to encode first downlink control information (DCI) and a second encoding scheme used to encode second DCI, and monitoring one or more first decoding candidates for the first DCI based on the first encoding scheme and one or more second decoding candidate for the second DCI based on the second encoding scheme.

25 Claims, 9 Drawing Sheets

(51) Int. Cl.
*G06F 16/28* (2019.01)
*H01J 49/00* (2006.01)
*H01J 49/16* (2006.01)
*H01J 49/42* (2006.01)
*G06F 19/00* (2018.01)
*G16H 50/70* (2018.01)

(52) U.S. Cl.
CPC ........ *H01J 49/0036* (2013.01); *H01J 49/165* (2013.01); *H01J 49/424* (2013.01); *G01N 2560/00* (2013.01); *G01N 2570/00* (2013.01); *G01N 2800/2835* (2013.01); *G06F 19/324* (2013.01); *G16H 50/70* (2018.01)

(56) References Cited

U.S. PATENT DOCUMENTS

| | | | | |
|---|---|---|---|---|
| 2010/0265862 A1* | 10/2010 | Choi | ............. | H04W 52/143 370/311 |
| 2013/0051342 A1* | 2/2013 | Aiba | ............. | H04L 1/1893 370/329 |
| 2013/0258989 A1* | 10/2013 | Ribeiro | ............. | H04W 16/14 370/329 |
| 2013/0279462 A1* | 10/2013 | He | ............. | H04W 72/0413 370/329 |
| 2014/0185540 A1 | 7/2014 | Gaal et al. | | |
| 2015/0043396 A1* | 2/2015 | Ekpenyong | ............. | H04L 5/1469 370/280 |
| 2015/0372784 A1* | 12/2015 | Xu | ............. | H04L 27/36 370/329 |
| 2016/0219600 A1* | 7/2016 | Li | ............. | H04W 72/1231 |
| 2017/0171897 A1* | 6/2017 | Ryu | ............. | H04L 5/0044 |
| 2017/0279472 A1* | 9/2017 | Wong | ............. | H04B 1/06 |
| 2018/0019843 A1* | 1/2018 | Papasakellariou | .... | H04L 1/1861 |
| 2018/0152954 A1* | 5/2018 | Golitschek Edler Von Elbwart | ............. | H04W 74/0808 |
| 2018/0351579 A1* | 12/2018 | Hong | ............. | H03M 13/13 |
| 2019/0140784 A1* | 5/2019 | Xi | ............. | H04L 1/0063 |

OTHER PUBLICATIONS

International Search Report and Written Opinion—PCT/US2017/039531, International Search Authority—European Patent Office, dated Nov. 9, 2017.
NTT DOCOMO et al., "Search Space Design", 3GPP Draft; R1-1708465, 3rd Generation Partnership Project (3GPP), Mobile Competence Centre ; 650, Route Des Lucioles ; F-06921 Sophia Antipolis Cedex; France, vol. RAN WG1, No. Hangzhou; May 15, 2017—May 19, 2017, May 6, 2017 (May 6, 2017), XP051262468, Retrieved from the Internet: URL: http://www.3gpp.org/ftp/tsg_ran/WG1_RL1/TSGR1_89/Docs/ [retrieved on May 6, 2017], pp. 1-3.
Partial International Search Report—PCT/US2017/039531—ISA/EPO—dated Sep. 18, 2017.

* cited by examiner

MONITORING CONTROL CHANNEL WITH DIFFERENT ENCODING SCHEMES

CLAIM OF PRIORITY UNDER 35 U.S.C. § 119

The present application claims the benefit of U.S. Provisional Patent Application Ser. No. 62/365,818, entitled "MONITORING CONTROL CHANNEL WITH DIFFERENT ENCODING SCHEMES" and filed Jul. 22, 2016, which is assigned to the assignee of the present application and hereby expressly incorporated by reference herein in its entirety.

INTRODUCTION

Aspects of the present disclosure are related generally to wireless communications systems, and more particularly, channel decoding.

Wireless communication systems are widely deployed to provide various telecommunication services such as telephony, video, data, messaging, and broadcasts. Typical wireless communication systems may employ multiple-access technologies capable of supporting communication with multiple users by sharing available system resources (e.g., bandwidth, transmit power). Examples of such multiple-access technologies include code division multiple access (CDMA) systems, time division multiple access (TDMA) systems, frequency division multiple access (FDMA) systems, orthogonal frequency division multiple access (OFDMA) systems, single-carrier frequency division multiple access (SC-FDMA) systems, and time division synchronous code division multiple access (TD-SCDMA) systems.

A wireless communication network may include a number of eNodeBs that can support communication for a number of user equipments (UEs). A UE may communicate with an eNodeB via the downlink and uplink. The downlink (or forward link) refers to the communication link from the eNodeB to the UE, and the uplink (or reverse link) refers to the communication link from the UE to the eNodeB.

These multiple access technologies have been adopted in various telecommunication standards to provide a common protocol that enables different wireless devices to communicate on a municipal, national, regional, and even global level. An example of an emerging telecommunication standard is Long Term Evolution (LTE). LTE is a set of enhancements to the Universal Mobile Telecommunications System (UMTS) mobile standard promulgated by Third Generation Partnership Project (3GPP). It is designed to better support mobile broadband Internet access by improving spectral efficiency, lower costs, improve services, make use of new spectrum, and better integrate with other open standards using OFDMA on the downlink (DL), SC-FDMA on the uplink (UL), and multiple-input multiple-output (MIMO) antenna technology. However, as the demand for mobile broadband access continues to increase, there exists a need for further improvements in LTE technology. Preferably, these improvements should be applicable to other multi-access technologies and the telecommunication standards that employ these technologies.

SUMMARY

The systems, methods, and devices of the disclosure each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features of this disclosure provide advantages that include improved communications between access points and stations in a wireless network.

Aspects of the present disclosure are generally directed to techniques for channel decoding using different encoding schemes.

Certain aspects of the present disclosure provide a method for wireless communications. The method may be performed, for example, by a user equipment (UE). The method generally includes determining a first encoding scheme used to encode first downlink control information (DCI) and a second encoding scheme used to encode second DCI, and monitoring one or more first decoding candidates for the first DCI based on the first encoding scheme and one or more second decoding candidate for the second DCI based on the second encoding scheme.

Certain aspects of the present disclosure provide a method for wireless communications. The method may be performed, for example, by a base station. The method generally includes determining a first encoding scheme and a second encoding scheme, selecting a first decoding candidate for a first DCI and a second decoding candidate for a second DCI, and transmitting, to a user equipment, the first decoding candidate for the first DCI using the first encoding scheme and the second decoding candidate for the second DCI using the second encoding scheme.

Certain aspects of the present disclosure provide an apparatus for wireless communication. The apparatus generally includes means for determining a first encoding scheme used to encode first DC) and a second encoding scheme used to encode second DCI, and means for monitoring one or more first decoding candidates for the first DCI based on the first encoding scheme and one or more second decoding candidates for the second DCI based on the second encoding scheme.

Certain aspects of the present disclosure provide an apparatus for wireless communication. The apparatus generally includes means for determining a first encoding scheme and a second encoding scheme, means for selecting a first decoding candidate for a first DCI and a second decoding candidate for a second DCI, and means for transmitting, to a UE, the first decoding candidate for the first DCI using the first encoding scheme and the second decoding candidate for the second DCI using the second encoding scheme.

Certain aspects of the present disclosure provide a UE. The UE generally includes a processing system for determining a first encoding scheme used to encode first DCI and a second encoding scheme used to encode second DCI, and a communication interface for monitoring one or more first decoding candidates for the first DCI based on the first encoding scheme and one or more second decoding candidate for the second DCI based on the second encoding scheme.

Certain aspects of the present disclosure provide a base station. The base station generally includes a processing system for determining a first encoding scheme and a second encoding scheme, and selecting a first decoding candidate for a first DCI and a second decoding candidate for a second DCI, and a communication interface for transmitting, to a UE, the first decoding candidate for the first DCI using the first encoding scheme and the second decoding candidate for the second DCI using the second encoding scheme.

Certain aspects of the present disclosure provide a computer-readable medium having instructions stored for determining a first encoding scheme used to encode first DCI and a second encoding scheme used to encode second DCI, and monitoring one or more first decoding candidates for the first DCI based on the first encoding scheme and one or more second decoding candidate for the second DCI based on the second encoding scheme.

Certain aspects of the present disclosure provide a computer-readable medium having instructions stored for determining a first encoding scheme and a second encoding scheme, selecting a first decoding candidate for a first DCI and a second decoding candidate for a second DCI, and transmitting, to a user equipment, the first decoding candidate for the first DCI using the first encoding scheme and the second decoding candidate for the second DCI using the second encoding scheme.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Figure 1:
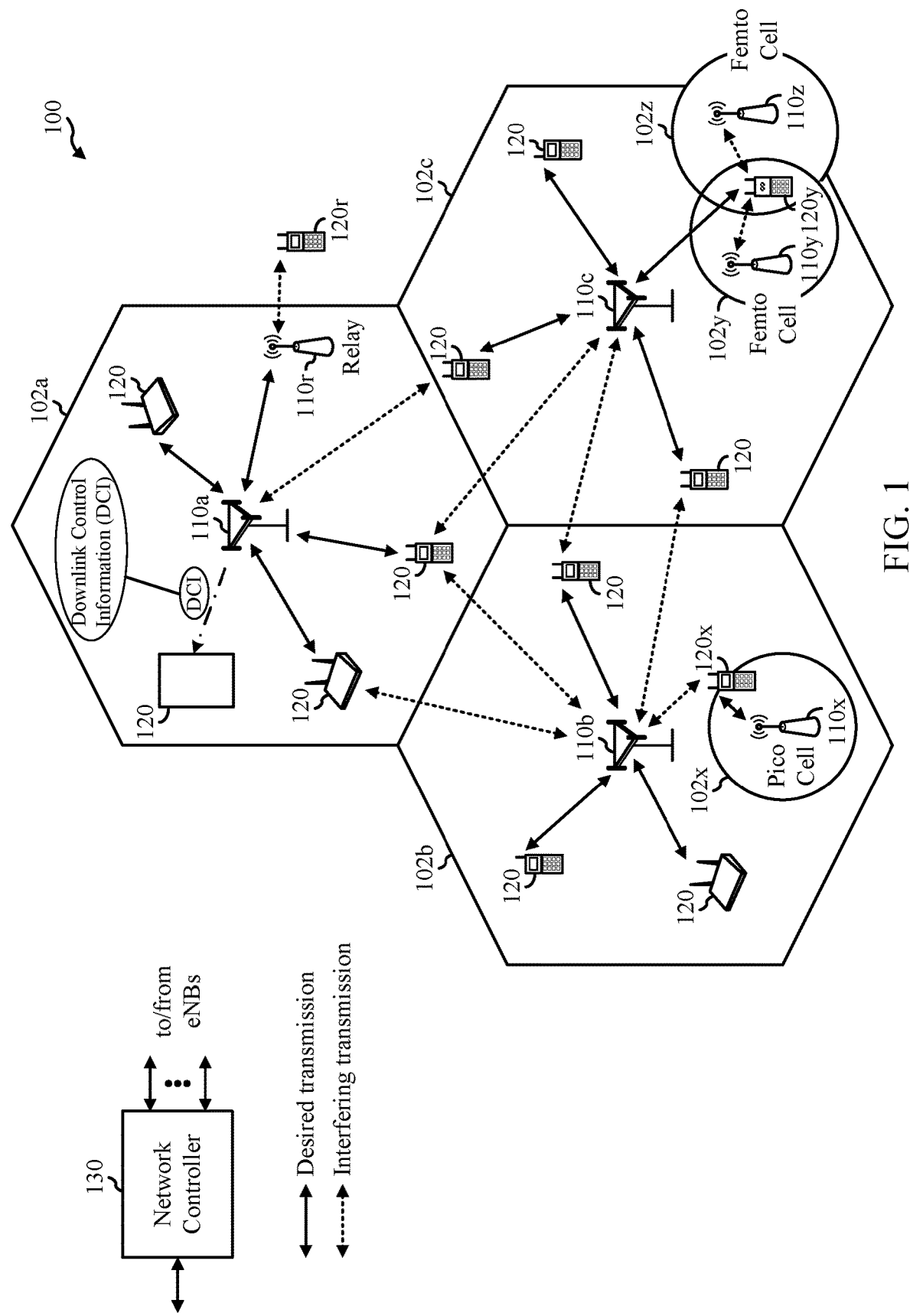
FIG. 1 is a block diagram conceptually illustrating an example telecommunications system, according to certain aspects of the present disclosure.

Certain aspects of the present disclosure provide apparatus, methods, processing systems, and computer-readable medium for channel decoding using different encoding schemes and may be applied to new radio (NR) access technology. NR may refer to radios configured to operate according to a new air interface (e.g., other than Orthogonal Frequency Divisional Multiple Access (OFDMA)-based air interfaces) or fixed transport layer (e.g., other than Internet Protocol (IP)). NR may include Enhanced mobile broadband (eMBB) targeting wide bandwidth (e.g. 80 MHz beyond), millimeter wave (mmW) targeting high carrier frequency (e.g. 60 GHz), massive MTC (mMTC) targeting non-backward compatible MTC techniques, and mission critical targeting ultra-reliable low latency communications (URLLC). For these general topics, different techniques are considered, such as coding, low-density parity check (LDPC), and polar. NR cell may refer to a cell operating according to the new air interface or fixed transport layer. A NR eNodeB may correspond to one or multiple transmission reception points (TRPs).

NR cells can be configured as access cell (ACells) or data only cells (DCells). For example, the RAN (e.g., a central unit or distributed unit) can configure the cells. DCells may be cells used for carrier aggregation or dual connectivity, but not used for initial access, cell selection/reselection, or handover. In some cases DCells may not transmit synchronization signals—in some cases DCells may transmit SS. TRPs may transmit downlink signals to UEs indicating the cell type. Based on the cell type indication, the UE may communicate with the TRP. For example, the UE may determine TRPs to consider for cell selection, access, handover, and/or measurement based on the indicated cell type.

In some cases, the UE can receive measurement configuration from the RAN. The measurement configuration information may indicate ACells or DCells for the UE to measure. The UE may monitor/detect measurement reference signals from the cells based on measurement configuration information. In some cases, the UE may blindly detect MRS. In some cases the UE may detect MRS based on MRS-IDs indicated from the RAN. The UE may report the measurement results.

In certain aspects of the present disclosure, the UE may monitor for downlink control information (DCI) assuming different encoding schemes. In some aspects, the encoding schemes may include tail-biting convolution code (TBCC) or polar coding. For example, the UE may be configured to monitor one or more decoding candidates for DCI using different encoding schemes and may determine the encoding schemes based on an indication from a base station or a pre-determined policy.

The determination of the encoding schemes used to monitor the decoding candidates may be based on different factors. For example, the encoding schemes may be determined based on a type of search space corresponding to the decoding candidates, the size and/or format of the DCI, a type or category of the UE, a type of radio network temporary identifier (RNTI) associated with the DCI, a duration of the control channel and/or a component carrier (CC) used to transmit the DCI.

In some cases, an encoding scheme used to monitor a data channel may be linked to an encoding scheme used to monitor the control channel. For example, if TBCC is used to monitor the control channel, low-density parity-check (LDPC) or turbo coding may be used to monitor the data channel. In some cases, the determination of the encoding scheme for monitoring the data channel may also depend on a payload range of the data channel.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting and the scope of the disclosure is being defined by the appended claims and equivalents thereof.

The techniques described herein may be used for various wireless communication networks such as CDMA, TDMA, FDMA, OFDMA, SC-FDMA and other networks. The terms "network" and "system" are often used interchangeably. A CDMA network may implement a radio technology such as Universal Terrestrial Radio Access (UTRA), cdma2000, etc. UTRA includes Wideband CDMA (WCDMA) and other variants of CDMA. cdma2000 covers IS-2000, IS-95 and IS-856 standards. A TDMA network may implement a radio technology such as Global System for Mobile Communications (GSM). An OFDMA network may implement a radio technology such as Evolved UTRA (E-UTRA), Ultra Mobile Broadband (UMB), IEEE 802.11 (Wi-Fi), IEEE 802.16 (WiMAX), IEEE 802.20, Flash-OFDMA, etc. UTRA and E-UTRA are part of Universal Mobile Telecommunication System (UMTS). 3GPP Long Term Evolution (LTE) and LTE-Advanced (LTE-A) are new releases of UMTS that use E-UTRA. UTRA, E-UTRA, UMTS, LTE, LTE-A and GSM are described in documents from an organization named "3rd Generation Partnership Project" (3GPP). cdma2000 and UMB are described in documents from an organization named "3rd Generation Partnership Project 2" (3GPP2). The techniques described herein may be used for the wireless networks and radio technologies mentioned above as well as other wireless networks and radio technologies. For clarity, certain aspects of the techniques are described below for LTE, and LTE terminology is used in much of the description below.

It is noted that while aspects may be described herein using terminology commonly associated with 3G and/or 4G wireless technologies, aspects of the present disclosure can be applied in other generation-based communication systems, such as 5G and later, including NR technologies.

Example Wireless Communications System

FIG. 1 illustrates an example wireless network 100 in which aspects of the present disclosure may be performed. For example, the wireless network may be NR or 5G network. The system illustrated in FIG. 1 may be, for example, a long term evolution (LTE) network or an NR network. The wireless network 100 may include a number of evolved Node Bs (eNodeBs) 110 and other network entities. An eNodeB may be a station that communicates with the UEs and may also be referred to as a base station, an access point, etc. A Node B is another example of a station that communicates with the UEs.

UEs 120 may be configured to perform the operations 900 discussed in more detail below for monitoring decoding candidates assuming different encoding schemes. eNodeB 110 may comprise the transmission reception point (TRP) configured to perform the operations 1000 discussed in more detail below for transmitting decoding candidates using different encoding schemes.

According to certain aspects, the eNodeB 110 and UEs 120 may be configured to perform operations related to determination of encoding schemes for transmission and decoding of DCI. For example, the eNodeB 110 may determine different encoding schemes for encoding and transmitting DCI to the UE 120, as illustrated. The UE 120 may also determine the encoding scheme and monitor one or more decoding candidates for the DCI. The determination of the encoding schemes by the eNodeB 110 and UE 120 may be based on a several factors, which are described in more detail herein.

Each eNodeB 110 may provide communication coverage for a particular geographic area. In 3GPP, the term "cell" can refer to a coverage area of an eNodeB and/or an eNodeB subsystem serving this coverage area, depending on the context in which the term is used.

An eNodeB may provide communication coverage for a macro cell, a pico cell, a femto cell, and/or other types of cell. A macro cell may cover a relatively large geographic area (e.g., several kilometers in radius) and may allow unrestricted access by UEs with service subscription. A pico cell may cover a relatively small geographic area and may allow unrestricted access by UEs with service subscription. A femto cell may cover a relatively small geographic area (e.g., a home) and may allow restricted access by UEs having association with the femto cell (e.g., UEs in a Closed Subscriber Group (CSG), UEs for users in the home, etc.). An eNB for a macro cell may be referred to as a macro eNodeB. An eNodeB for a pico cell may be referred to as a pico eNB. An eNodeB for a femto cell may be referred to as a femto eNB or a home eNB. In the example shown in FIG. 1, the eNodeBs 110a, 110b and 110c may be macro eNodeBs for the macro cells 102a, 102b and 102c, respectively. The eNodeB 110x may be a pico eNodeB for a pico cell 102x. The eNodeBs 110y and 110z may be femto eNodeBs for the femto cells 102y and 102z, respectively. An eNodeB may support one or multiple (e.g., three) cells.

The wireless network 100 may also include relay stations. A relay station is a station that receives a transmission of data and/or other information from an upstream station (e.g., an eNodeB or a UE) and sends a transmission of the data and/or other information to a downstream station (e.g., a UE or an eNodeB). A relay station may also be a UE that relays transmissions for other UEs. In the example shown in FIG. 1, a relay station 110r may communicate with the eNodeB 110a and a UE 120r in order to facilitate communication between the eNodeB 110a and the UE 120r. A relay station may also be referred to as a relay eNodeB, a relay, etc.

The wireless network 100 may be a heterogeneous network that includes eNodeBs of different types, e.g., macro eNodeBs, pico eNodeBs, femto eNodeBs, relays, transmission reception points (TRPs), etc. These different types of eNodeBs may have different transmit power levels, different coverage areas, and different impact on interference in the wireless network 100. For example, macro eNodeBs may have a high transmit power level (e.g., 20 Watts) whereas pico eNodeBs, femto eNodeBs and relays may have a lower transmit power level (e.g., 1 Watt).

The wireless network 100 may support synchronous or asynchronous operation. For synchronous operation, the eNodeBs may have similar frame timing, and transmissions from different eNodeBs may be approximately aligned in time. For asynchronous operation, the eNodeBs may have different frame timing, and transmissions from different eNodeBs may not be aligned in time. The techniques described herein may be used for both synchronous and asynchronous operation.

A network controller 130 may couple to a set of eNodeBs and provide coordination and control for these eNodeBs. The network controller 130 may communicate with the eNodeBs 110 via a backhaul. The eNodeBs 110 may also communicate with one another, e.g., directly or indirectly via wireless or wireline backhaul.

The UEs 120 (e.g., 120x, 120y, etc.) may be dispersed throughout the wireless network 100, and each UE may be stationary or mobile. A UE may also be referred to as a terminal, a mobile station, a subscriber unit, a station, etc. A UE may be a cellular phone, a personal digital assistant (PDA), a wireless modem, a wireless communication device, a handheld device, a laptop computer, a cordless phone, a wireless local loop (WLL) station, a tablet, a netbook, a smart book, etc. A UE may be able to communicate with macro eNodeBs, pico eNodeBs, femto eNodeBs, relays, etc. In FIG. 1, a solid line with double arrows indicates desired transmissions between a UE and a serving eNodeB, which is an eNodeB designated to serve the UE on the downlink and/or uplink. A dashed line with double arrows indicates interfering transmissions between a UE and an eNodeB.

LTE utilizes orthogonal frequency division multiplexing (OFDM) on the downlink and single-carrier frequency division multiplexing (SC-FDM) on the uplink. OFDM and SC-FDM partition the system bandwidth into multiple (K) orthogonal subcarriers, which are also commonly referred to as tones, bins, etc. Each subcarrier may be modulated with data. In general, modulation symbols are sent in the frequency domain with OFDM and in the time domain with SC-FDM. The spacing between adjacent subcarriers may be fixed, and the total number of subcarriers (K) may be dependent on the system bandwidth. For example, the spacing of the subcarriers may be 15 kHz and the minimum resource allocation (called a 'resource block') may be 12 subcarriers (or 180 kHz). Consequently, the nominal FFT size may be equal to 128, 256, 512, 1024 or 2048 for system bandwidth of 1.25, 2.5, 5, 10 or 20 megahertz (MHz), respectively. The system bandwidth may also be partitioned into subbands. For example, a subband may cover 1.08 MHz (i.e., 6 resource blocks), and there may be 1, 2, 4, 8 or 16 subbands for system bandwidth of 1.25, 2.5, 5, 10 or 20 MHz, respectively. New radio (NR) may use a different air interface, other than OFDM-based. NR networks may include entities such central units or distributed units.

Figure 2:
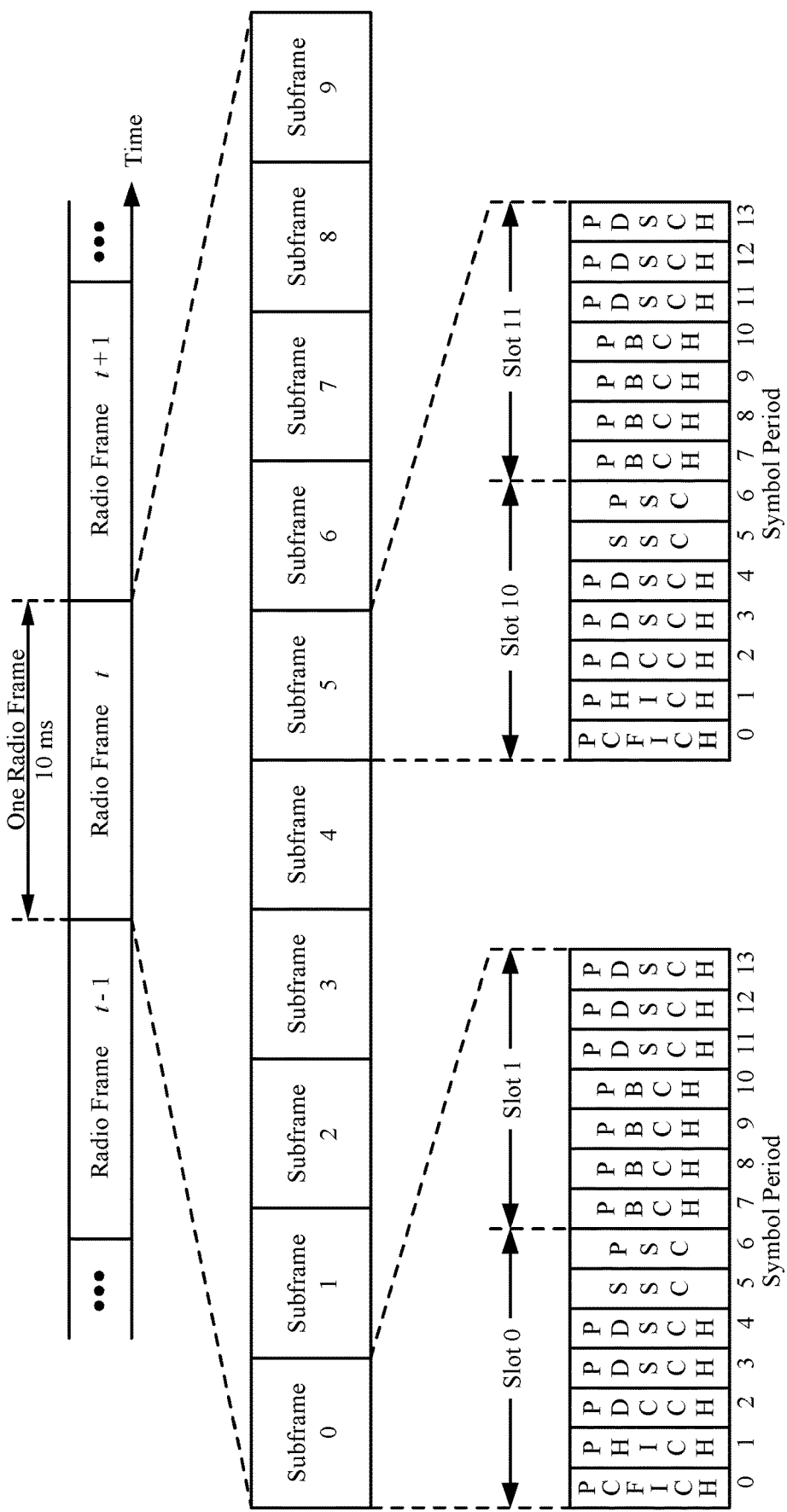
FIG. 2 is a block diagram conceptually illustrating an example downlink frame structure in a telecommunications system, according to certain aspects of the present disclosure.

FIG. 2 shows a down link (DL) frame structure used in a telecommunication systems (e.g., LTE). The transmission timeline for the downlink may be partitioned into units of radio frames. Each radio frame may have a predetermined duration (e.g., 10 milliseconds (ms)) and may be partitioned into 10 sub-frames with indices of 0 through 9. Each sub-frame may include two slots. Each radio frame may thus include 20 slots with indices of 0 through 19. Each slot may include L symbol periods, e.g., 7 symbol periods for a normal cyclic prefix (as shown in FIG. 2) or 14 symbol periods for an extended cyclic prefix. The 2L symbol periods in each sub-frame may be assigned indices of 0 through 2L−1. The available time frequency resources may be partitioned into resource blocks. Each resource block may cover N subcarriers (e.g., 12 subcarriers) in one slot.

In LTE, an eNodeB may send a primary synchronization signal (PSS) and a secondary synchronization signal (SSS) for each cell in the eNodeB. The primary and secondary synchronization signals may be sent in symbol periods 6 and 5, respectively, in each of sub-frames 0 and 5 of each radio frame with the normal cyclic prefix, as shown in FIG. 2. The synchronization signals may be used by UEs for cell detection and acquisition. The eNodeB may send a Physical Broadcast Channel (PBCH) in symbol periods 0 to 3 in slot 1 of sub-frame 0. The PBCH may carry certain system information.

The eNodeB may send a Physical Control Format Indicator Channel (PCFICH) in only a portion of the first symbol period of each sub-frame, although depicted in the entire first symbol period in FIG. 2. The PCFICH may convey the number of symbol periods (M) used for control channels, where M may be equal to 1, 2 or 3 and may change from sub-frame to sub-frame. M may also be equal to 4 for a small system bandwidth, e.g., with less than 10 resource blocks. In the example shown in FIG. 2, M=3. The eNodeB may send a Physical HARQ Indicator Channel (PHICH) and a Physical Downlink Control Channel (PDCCH) in the first M symbol periods of each sub-frame (M=3 in FIG. 2). The PHICH may carry information to support hybrid automatic retransmission (HARQ). The PDCCH may carry information on uplink and downlink resource allocation for UEs and power control information for uplink channels. Although not shown in the first symbol period in FIG. 2, it is understood that the PDCCH and PHICH are also included in the first symbol period. Similarly, the PHICH and PDCCH are also both in the second and third symbol periods, although not shown that way in FIG. 2. The eNodeB may send a Physical Downlink Shared Channel (PDSCH) in the remaining symbol periods of each sub-frame. The PDSCH may carry data for UEs scheduled for data transmission on the downlink. The various signals and channels in LTE are described in 3GPP TS 36.211, entitled "Evolved Universal Terrestrial Radio Access (E-UTRA); Physical Channels and Modulation," which is publicly available.

The eNodeB may send the PSS, SSS and PBCH in the center 1.08 MHz of the system bandwidth used by the eNodeB. The eNodeB may send the PCFICH and PHICH across the entire system bandwidth in each symbol period in which these channels are sent. The eNodeB may send the PDCCH to groups of UEs in certain portions of the system bandwidth. The eNodeB may send the PDSCH to specific UEs in specific portions of the system bandwidth. The eNodeB may send the PSS, SSS, PBCH, PCFICH and PHICH in a broadcast manner to all UEs, may send the PDCCH in a unicast manner to specific UEs, and may also send the PDSCH in a unicast manner to specific UEs.

A number of resource elements may be available in each symbol period. Each resource element may cover one subcarrier in one symbol period and may be used to send one modulation symbol, which may be a real or complex value. Resource elements not used for a reference signal in each symbol period may be arranged into resource element groups (REGs). Each REG may include four resource elements in one symbol period. The PCFICH may occupy four REGs, which may be spaced approximately equally across frequency, in symbol period 0. The PHICH may occupy three REGs, which may be spread across frequency, in one or more configurable symbol periods. For example, the three REGs for the PHICH may all belong in symbol period 0 or may be spread in symbol periods 0, 1 and 2. The PDCCH may occupy 9, 18, 32 or 64 REGs, which may be selected from the available REGs, in the first M symbol periods. Only certain combinations of REGs may be allowed for the PDCCH.

A UE may know the specific REGs used for the PHICH and the PCFICH. The UE may search different combinations of REGs for the PDCCH. The number of combinations to search is typically less than the number of allowed combinations for the PDCCH. An eNodeB may send the PDCCH to the UE in any of the combinations that the UE will search.

A UE may be within the coverage of multiple eNodeBs. One of these eNodeBs may be selected to serve the UE. The serving eNodeB may be selected based on various criteria such as received power, path loss, signal-to-noise ratio (SNR), etc.

Figure 3:
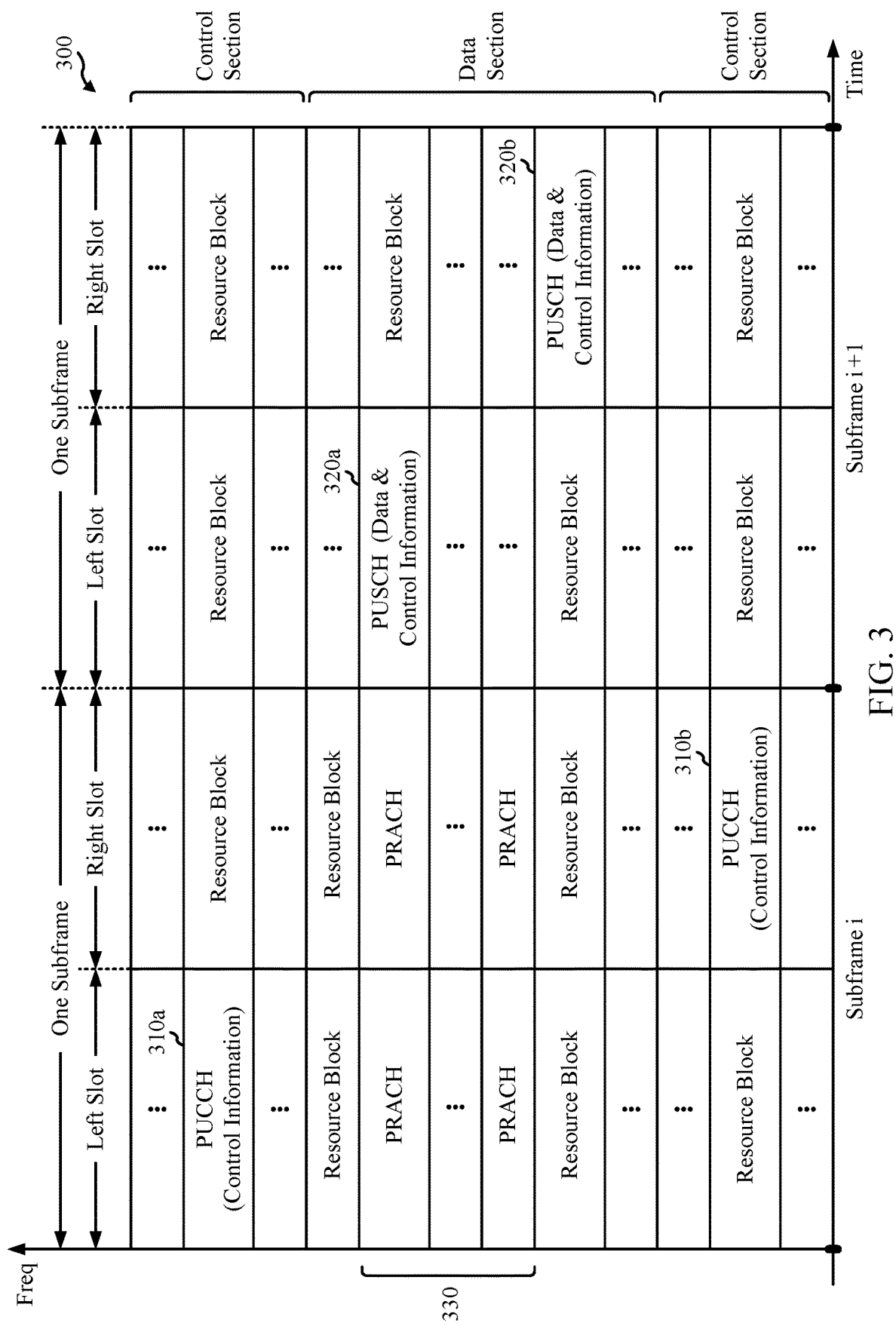
FIG. 3 is a diagram illustrating an example uplink frame structure in a telecommunications system, according to certain aspects of the present disclosure.

FIG. 3 is a diagram 300 illustrating an example of an uplink (UL) frame structure in a telecommunications system (e.g., LTE). The available resource blocks for the UL may be partitioned into a data section and a control section. The control section may be formed at the two edges of the system bandwidth and may have a configurable size. The resource blocks in the control section may be assigned to UEs for transmission of control information. The data section may include all resource blocks not included in the control section. The UL frame structure results in the data section including contiguous subcarriers, which may allow a single UE to be assigned all of the contiguous subcarriers in the data section.

A UE may be assigned resource blocks 310a, 310b in the control section to transmit control information to an eNodeB. The UE may also be assigned resource blocks 320a, 320b in the data section to transmit data to the eNodeB. The UE may transmit control information in a physical UL control channel (PUCCH) on the assigned resource blocks in the control section. The UE may transmit only data or both data and control information in a physical UL shared channel (PUSCH) on the assigned resource blocks in the data section. A UL transmission may span both slots of a subframe and may hop across frequency.

A set of resource blocks may be used to perform initial system access and achieve UL synchronization in a physical random access channel (PRACH) 330. The PRACH 330 carries a random sequence and cannot carry any UL data/signaling. Each random access preamble occupies a bandwidth corresponding to six consecutive resource blocks. The starting frequency is specified by the network. That is, the transmission of the random access preamble is restricted to certain time and frequency resources. There is no frequency hopping for the PRACH. The PRACH attempt is carried in a single subframe (1 ms) or in a sequence of few contiguous subframes and a UE can make only a single PRACH attempt per frame (10 ms).

Figure 4:
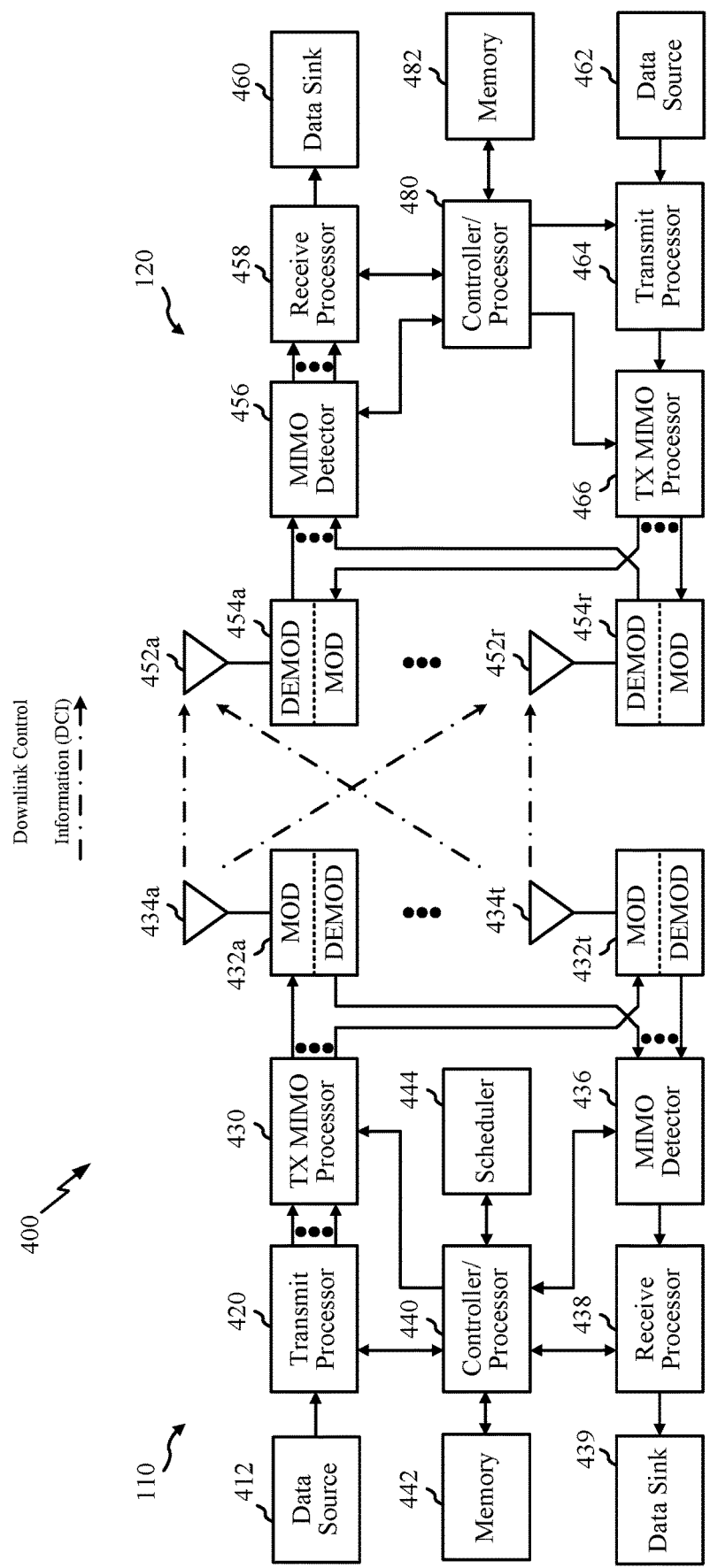
FIG. 4 is a block diagram conceptually illustrating a design of example eNodeB and user equipment (UE), according to certain aspects of the present disclosure.

FIG. 4 illustrates example components of the base station/eNodeB 110 and UE 120 illustrated in FIG. 1, which may be used to implement aspects of the present disclosure. One or more components of the AP 110 and UE 120 may be used to practice aspects of the present disclosure. For example, antennas 452, Tx/Rx 222, processors 466, 458, 464, and/or controller/processor 480 of the UE 120 and/or antennas 434, processors 460, 420, 438, and/or controller/processor 440 of the eNodeB 110 may be used to perform the operations described herein and illustrated with reference to FIGS. 9-10.

According to certain aspects, a processor (e.g., processor 440) of the eNodeB 110 and a process (e.g., processors 480) of the UE 120 may determine different encoding schemes for transmission and decoding of DCI. The DCI may be transmitted by antennas 434 of the eNodeB 110 and received by antennas 452 of UE 120. For example, the UE 120 may monitor one or more decoding candidates for the DCI based on a determination of an encoding scheme used by the eNodeB 110 to encode the DCI. The determination of the encoding scheme by the eNodeB 110 and UE 120 may be based on a several factors, which are described in more detail herein.

FIG. 4 shows a block diagram of a design of a base station/eNodeB 110 and a UE 120, which may be one of the base stations/eNodeBs and one of the UEs in FIG. 1. For a restricted association scenario, the base station 110 may be the macro eNodeB 110c in FIG. 1, and the UE 120 may be the UE 120y. The base station 110 may also be a base station of some other type. The base station 110 may be equipped with antennas 434a through 434t, and the UE 120 may be equipped with antennas 452a through 452r.

At the base station 110, a transmit processor 420 may receive data from a data source 412 and control information from a controller/processor 440. The control information may be for the PBCH, PCFICH, PHICH, PDCCH, etc. The data may be for the PDSCH, etc. The processor 420 may process (e.g., encode and symbol map) the data and control information to obtain data symbols and control symbols, respectively. The processor 420 may also generate reference symbols, e.g., for the PSS, SSS, and cell-specific reference signal. A transmit (TX) multiple-input multiple-output (MIMO) processor 430 may perform spatial processing (e.g., precoding) on the data symbols, the control symbols, and/or the reference symbols, if applicable, and may provide output symbol streams to the modulators (MODs) 432a through 432t. Each modulator 432 may process a respective output symbol stream (e.g., for OFDM, etc.) to obtain an output sample stream. Each modulator 432 may further process (e.g., convert to analog, amplify, filter, and upconvert) the output sample stream to obtain a downlink signal.

Downlink signals from modulators 432a through 432t may be transmitted via the antennas 434a through 434t, respectively.

At the UE 120, the antennas 452a through 452r may receive the downlink signals from the base station 110 and may provide received signals to the demodulators (DEMODs) 454a through 454r, respectively. Each demodulator 454 may condition (e.g., filter, amplify, downconvert, and digitize) a respective received signal to obtain input samples. Each demodulator 454 may further process the input samples (e.g., for OFDM, etc.) to obtain received symbols. A MIMO detector 456 may obtain received symbols from all the demodulators 454a through 454r, perform MIMO detection on the received symbols if applicable, and provide detected symbols. A receive processor 458 may process (e.g., demodulate, deinterleave, and decode) the detected symbols, provide decoded data for the UE 120 to a data sink 460, and provide decoded control information to a controller/processor 480.

On the uplink, at the UE 120, a transmit processor 464 may receive and process data (e.g., for the PUSCH) from a data source 462 and control information (e.g., for the PUCCH) from the controller/processor 480. The transmit processor 464 may also generate reference symbols for a reference signal. The symbols from the transmit processor 464 may be precoded by a TX MIMO processor 466 if applicable, further processed by the demodulators 454a through 454r (e.g., for SC-FDM, etc.), and transmitted to the base station 110. At the base station 110, the uplink signals from the UE 120 may be received by the antennas 434, processed by the modulators 432, detected by a MIMO detector 436 if applicable, and further processed by a receive processor 438 to obtain decoded data and control information sent by the UE 120. The receive processor 438 may provide the decoded data to a data sink 439 and the decoded control information to the controller/processor 440.

The controllers/processors 440 and 480 may direct the operation at the base station 110 and the UE 120, respectively. The processor 440 and/or other processors and modules at the base station 110 may perform or direct, e.g., the execution of various processes for the techniques described herein. The processor 480 and/or other processors and modules at the UE 120 may also perform or direct, e.g., the execution of the functional blocks illustrated in FIGS. 9-10, and/or other processes for the techniques described herein. The memories 442 and 482 may store data and program codes for the base station 110 and the UE 120, respectively. A scheduler 444 may schedule UEs for data transmission on the downlink and/or uplink.

Figure 5:
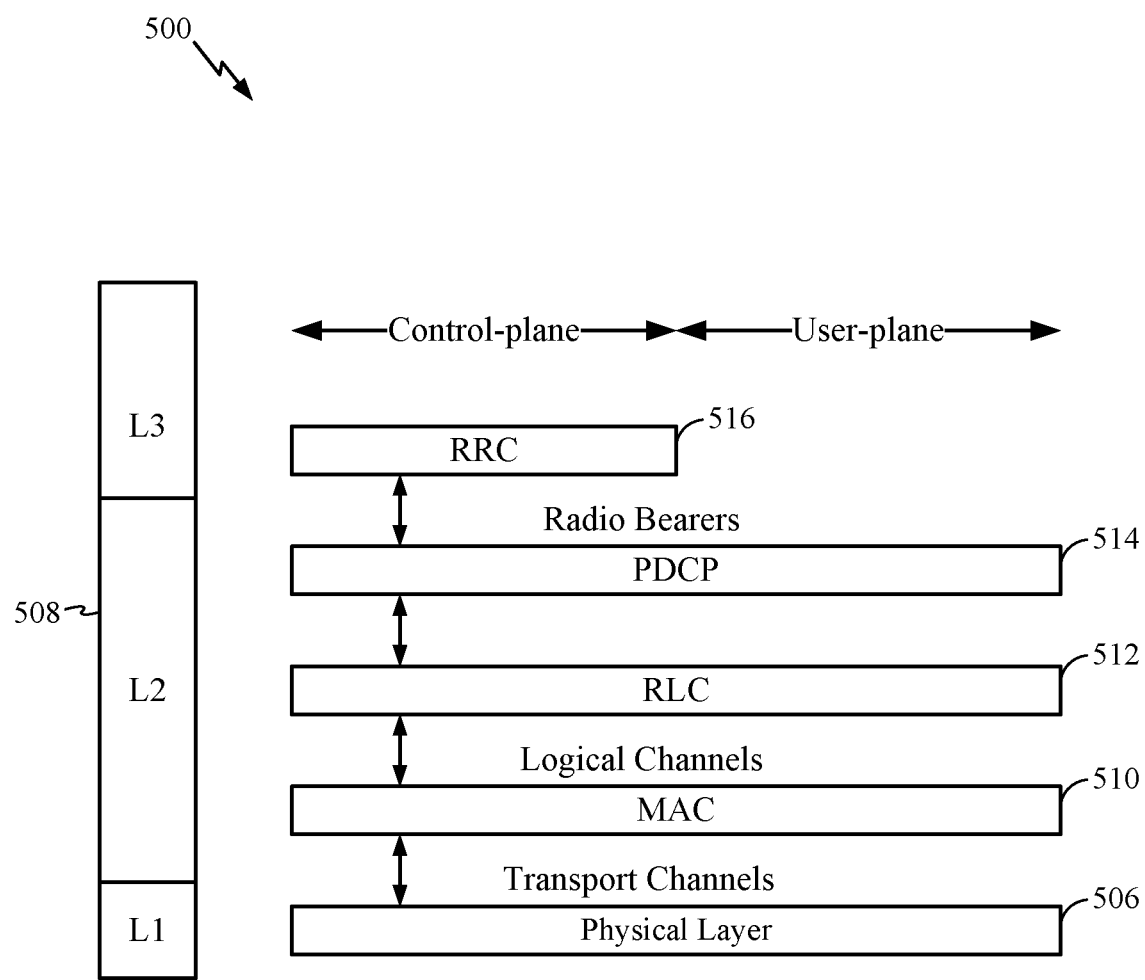
FIG. 5 is a diagram illustrating an example radio protocol architecture for the user and control planes, according to certain aspects of the present disclosure.

FIG. 5 is a diagram 500 illustrating an example of a radio protocol architecture for the user and control planes in LTE. The radio protocol architecture for the UE and the eNodeB is shown with three layers: Layer 1, Layer 2, and Layer 3. Layer 1 (L1 layer) is the lowest layer and implements various physical layer signal processing functions. The L1 layer will be referred to herein as the physical layer 506. Layer 2 (L2 layer) 508 is above the physical layer 506 and is responsible for the link between the UE and eNodeB over the physical layer 506.

In the user plane, the L2 layer 508 includes a media access control (MAC) sublayer 510, a radio link control (RLC) sublayer 512, and a packet data convergence protocol (PDCP) 514 sublayer, which are terminated at the eNodeB on the network side. Although not shown, the UE may have several upper layers above the L2 layer 508 including a network layer (e.g., IP layer) that is terminated at the PDN gateway 118 on the network side, and an application layer that is terminated at the other end of the connection (e.g., far end UE, server, etc.).

The PDCP sublayer 514 provides multiplexing between different radio bearers and logical channels. The PDCP sublayer 514 also provides header compression for upper layer data packets to reduce radio transmission overhead, security by ciphering the data packets, and handover support for UEs between eNodeBs. The RLC sublayer 512 provides segmentation and reassembly of upper layer data packets, retransmission of lost data packets, and reordering of data packets to compensate for out-of-order reception due to hybrid automatic repeat request (HARQ). The MAC sublayer 510 provides multiplexing between logical and transport channels. The MAC sublayer 510 is also responsible for allocating the various radio resources (e.g., resource blocks) in one cell among the UEs. The MAC sublayer 510 is also responsible for HARQ operations.

In the control plane, the radio protocol architecture for the UE and eNodeB is substantially the same for the physical layer 506 and the L2 layer 508 with the exception that there is no header compression function for the control plane. The control plane also includes a radio resource control (RRC) sublayer 516 in Layer 3 (L3 layer). The RRC sublayer 516 is responsible for obtaining radio resources (i.e., radio bearers) and for configuring the lower layers using RRC signaling between the eNodeB and the UE.

Figure 6:
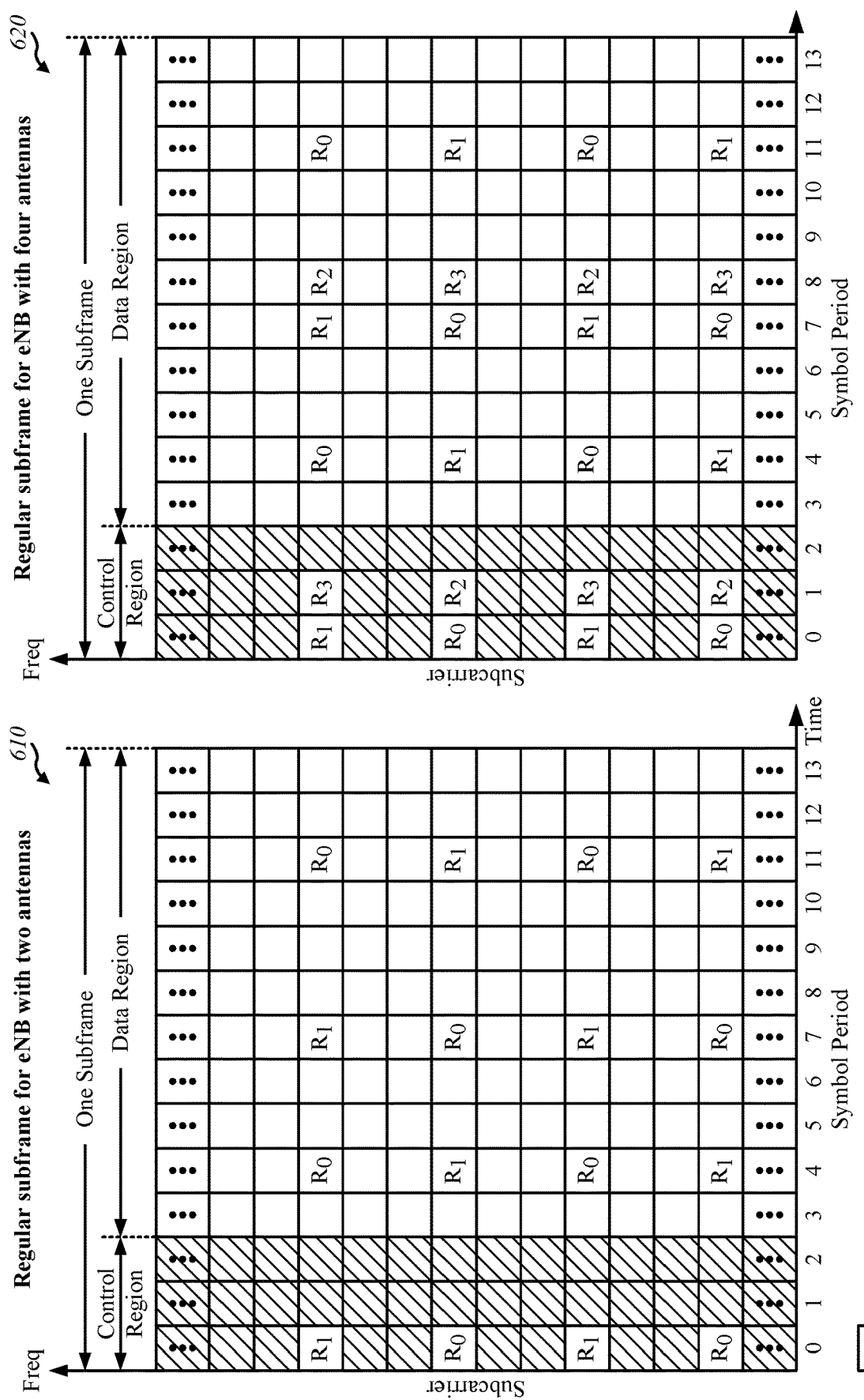
FIG. 6 illustrates an example subframe resource element mapping, according to certain aspects of the present disclosure.

FIG. 6 shows two exemplary subframe formats 610 and 620 for the downlink with the normal cyclic prefix. The available time frequency resources for the downlink may be partitioned into resource blocks. Each resource block may cover 12 subcarriers in one slot and may include a number of resource elements. Each resource element may cover one subcarrier in one symbol period and may be used to send one modulation symbol, which may be a real or complex value.

Subframe format 610 may be used for an eNodeB equipped with two antennas. A CRS may be transmitted from antennas 0 and 1 in symbol periods 0, 4, 7 and 11. A reference signal is a signal that is known a priori by a transmitter and a receiver and may also be referred to as a pilot. A CRS is a reference signal that is specific for a cell, e.g., generated based on a cell identity (ID). In FIG. 6, for a given resource element with label $R_a$, a modulation symbol may be transmitted on that resource element from antenna a, and no modulation symbols may be transmitted on that resource element from other antennas. Subframe format 620 may be used for an eNodeB equipped with four antennas. A CRS may be transmitted from antennas 0 and 1 in symbol periods 0, 4, 7 and 11 and from antennas 2 and 3 in symbol periods 1 and 8. For both subframe formats 610 and 620, a CRS may be transmitted on evenly spaced subcarriers, which may be determined based on cell ID. Different eNodeBs may transmit their CRSs on the same or different subcarriers, depending on their cell IDs. For both subframe formats 610 and 620, resource elements not used for the CRS may be used to transmit data (e.g., traffic data, control data, and/or other data).

The PSS, SSS, CRS and PBCH in LTE are described in 3GPP TS 36.211, entitled "Evolved Universal Terrestrial Radio Access (E-UTRA); Physical Channels and Modulation," which is publicly available.

An interlace structure may be used for each of the downlink and uplink for FDD in LTE. For example, Q interlaces with indices of 0 through Q−1 may be defined, where Q may be equal to 4, 6, 8, 10, or some other value. Each interlace may include subframes that are spaced apart by Q frames. In particular, interlace q may include subframes q, q+Q, q+2Q, etc., where q∈{0, . . . , Q−1}.

The wireless network may support hybrid automatic retransmission (HARQ) for data transmission on the downlink and uplink. For HARQ, a transmitter (e.g., an eNodeB) may send one or more transmissions of a packet until the packet is decoded correctly by a receiver (e.g., a UE) or some other termination condition is encountered. For synchronous HARQ, all transmissions of the packet may be sent in subframes of a single interlace. For asynchronous HARQ, each transmission of the packet may be sent in any subframe.

A UE may be located within the coverage area of multiple eNodeBs. One of these eNodeBs may be selected to serve the UE. The serving eNodeB may be selected based on various criteria such as received signal strength, received signal quality, pathloss, etc. Received signal quality may be quantified by a signal-to-noise-and-interference ratio (SINR), or a reference signal received quality (RSRQ), or some other metric. The UE may operate in a dominant interference scenario in which the UE may observe high interference from one or more interfering eNodeBs.

Example Carrier Aggregation

Figure 7:
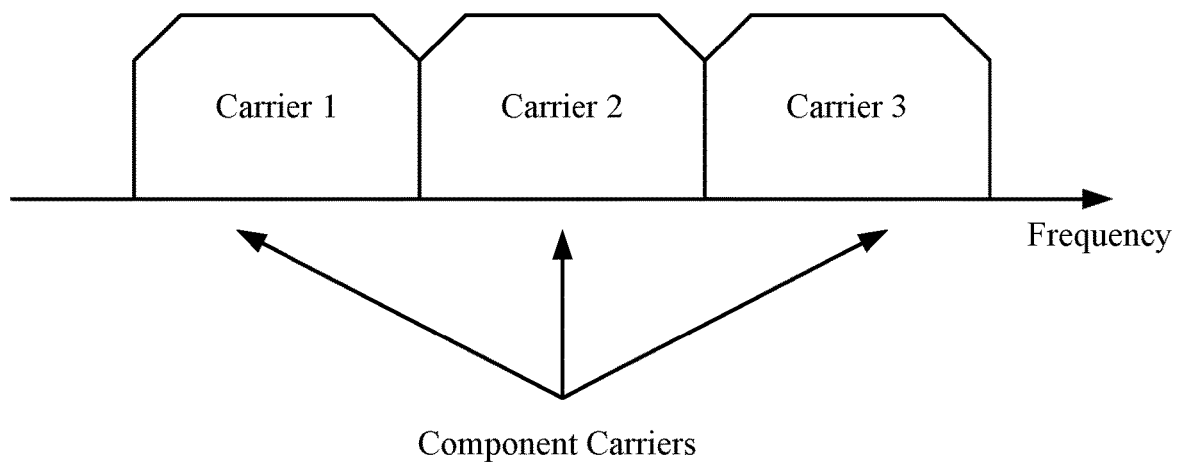
FIG. 7 illustrates an example continuous carrier aggregation type, according to certain aspects of the present disclosure.
Figure 8:
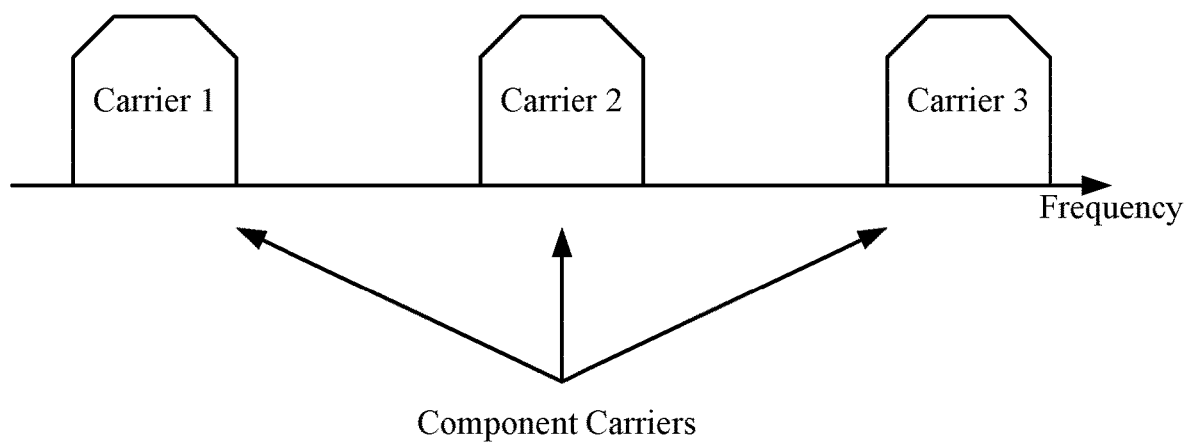
FIG. 8 illustrates an example non-continuous carrier aggregation type, according to certain aspects of the present disclosure.

Certain UEs may use spectrum of up to 20 MHz bandwidths allocated in a carrier aggregation of up to a total of 100 MHz (5 component carriers) used for transmission in each direction. For some mobile systems, two types of carrier aggregation (CA) methods have been proposed, continuous CA and non-continuous CA. They are illustrated in FIGS. 7 and 8. Continuous CA occurs when multiple available component carriers are adjacent to each other (FIG. 7). On the other hand, non-continuous CA occurs when multiple available component carriers are separated along the frequency band (FIG. 8). Both non-continuous and continuous CA aggregates multiple component carriers to serve a single UE.

According to various aspects, the UE operating in a multicarrier system (also referred to as carrier aggregation) is configured to aggregate certain functions of multiple carriers, such as control and feedback functions, on the same carrier, which may be referred to as a "primary carrier." The remaining carriers that depend on the primary carrier for support are referred to as associated secondary carriers. For example, the UE may aggregate control functions such as those provided by the optional dedicated channel (DCH), the nonscheduled grants, a physical uplink control channel (PUCCH), and/or a physical downlink control channel (PDCCH).

Example Dual Connectivity

Presently, mobiles devices (e.g., UEs) receive data from one base station (e.g., eNodeB). However, users on a cell edge may experience high inter-cell interference which may limit the data rates. Multiflow allows users to receive data from two eNodeBs simultaneously. For example, the UE sends and receives data from the two eNodeBs in two separate streams when the UE is in range of two cell towers in two adjacent cells at the same time. The UE communicates with the two towers simultaneously when the UE is on the edge of either towers' reach. By scheduling two independent data streams to the UE from two different eNodeBs at the same time, multiflow exploits uneven loading in networks. This helps improve the cell edge user experience while increasing network capacity. In one example, throughput data speeds for users at a cell edge may double. "Multiflow" is similar to dual-carrier HSPA, however, there are differences. For example, dual-carrier HSPA does not allow for connectivity to multiple towers to connect simultaneously to a device.

Dual connectivity may have benefits in the cellular industry. Dual Connectivity can significantly improve per-user throughput and mobility robustness by allowing users to be connected simultaneously to master cell group (MCG) and secondary cell group (SCG) via MeNodeB (master eNodeB) and SeNodeB (secondary eNodeB), respectively. The increase in per-user throughput is achieved by aggregating radio resources from at least two eNodeBs. Moreover, dual connectivity also helps in load balancing between MCG and SCG.

The MeNodeB and SeNodeB may not be collocated and can be connected via a non-ideal backhaul (e.g., backhaul). Thus, the different eNodeBs may use different schedulers, etc. For example, the UE may be dually connected to the a macro cell and the small cell, and the eNodeBs may be connected via a non-ideal backhaul and operate on different carrier frequencies. With carrier aggregation multiple LTE/component carriers are aggregated to serve a single unit of LTE Advanced UE.

In certain aspects, due to the distributed nature of this deployment scenario (separate eNodeBs connected via a non-ideal backhaul) separate uplink control channels for both eNodeBs (MeNodeB and SeNodeB) are used to support distributed scheduling and independent MAC (Medium Access Control) operation across eNodeBs. This is unlike CA (Carrier Aggregation) deployment, in which a single MAC/scheduling entity operates across all the carriers and a single uplink control channel is used.

In certain systems, the Primary Cell (PCell of MeNodeB) is the only cell carrying the uplink control channels (e.g., the PUCCH). For dual connectivity, a special cell on the SeNodeB may support the uplink control channels for the SeNodeB. Also, with dual connectivity uplink control channels for both the MeNodeB and the SeNodeB are used, one for each eNodeB.

Example Technique for Monitoring a Control Channel with Different Encoding Schemes Various coding schemes are being considered for new radio (NR). NR may refer to radios configured to operate according to a wireless standard, such as 5G (e.g. wireless network 100). NR may include Enhanced mobile broadband (eMBB) targeting wide bandwidth (e.g. 80 MHz beyond), millimeter wave (mmW) targeting high carrier frequency (e.g. 60 GHz), massive machine type communication (mMTC) targeting non-backward compatible MTC techniques, and mission critical targeting ultra-reliable low latency communications (URLLC). An NR cell may refer to a cell operating according to the NR network. A NR eNodeB (e.g., eNodeB 110) may correspond to one or multiple transmission reception points (TRPs). As used herein, a cell may refer to a combination of downlink (and potentially also uplink) resources.

Different encoding schemes may be used to encode decoding candidates for downlink control information (DCI), and each encoding scheme may have different pros and cons. For example, performance gain often comes with encoding/decoding complexity, and consequently, different impact on decoding latency. In NR, ultra-reliability low latency communications (URLLC) may be used that have a reliability in the order of $10^{-5}$ or lower.

In LTE, a control channel can be in the form of a physical downlink control channel (PDCCH), an enhanced PDCCH (EPDCCH), a machine-type PDCCH, (mPDCCH), or a shortened TTI PDCCH (sPDCCH), for example. These control channels may be associated with a search space including a set of decoding candidates that a UE monitors. Each decoding candidate may be associated with a certain aggregation level that may correspond to a certain number of resource elements, and there can be multiple aggregation levels. Each aggregation level may have one or more decoding candidates for a UE to monitor.

The search space may include a common search space (CSS) and a UE-specific search space (UESS). The CSS generally refers to a search space that is shared by all UEs (or a group of UEs) served by the same cell, while UESS generally refers to a search space that is specifically defined for a UE based on a UE-specific ID. The CSS may be used to carry control channels targeting broadcast/multicast/groupcast communications, and typically as a fallback, also unicast communications.

The control channel may also be associated with one or more DCI formats. Different DCI formats may be of the same or different sizes, targeting different purposes such as DL vs. UL grants, single-input multiple-output (SIMO) vs. multiple-input multiple-output (MIMO) scheduling, group power control commands. Moreover, one or more Radio Network Temporary Identifiers (RNTIs) may be associated with a control channel transmission. For example, the cyclic redundancy check (CRC) of the control channel may be scrambled based on the RNTI. The RNTIs may be non-UE-specific (e.g., CSS only), which may include system information RNTI (SI-RNTI), paging RNTI (P-RNTI), random access RNTI (RA-RNTI), Global System for Mobile communication (GSM) EDGE Radio Access Network (GERAN) RNTI (G-RNTI), system change RNTI (SC-RNTI), transmit power control (TPC) PUCCH/PUSCH RNTI, for example. In some cases, the RNTI may be UE-specific or UESS+CSS which includes cell-radio RNTI (C-RNTI), semi-persistent schedule RNTI (SPS-RNTI), for example.

In some cases, it may be desirable to employ an encoding scheme for ultra-reliable control channel transmission (e.g., for URLLC). In this case, polar coding encoding scheme may be used. However, such an encoding scheme may come with additional decoding complexity and decoding latency. Moreover, not all UEs use or are capable of using URLLC. In addition, polar coding encoding scheme may not exhibit a noticeable performance gain over tail-biting convolution code (TBCC) encoding scheme for a certain payload range, e.g., 20-40 bits.

Aspects of the present disclosure are directed to determining different encoding candidates for transmitting and monitoring decoding candidates.

Figure 9:
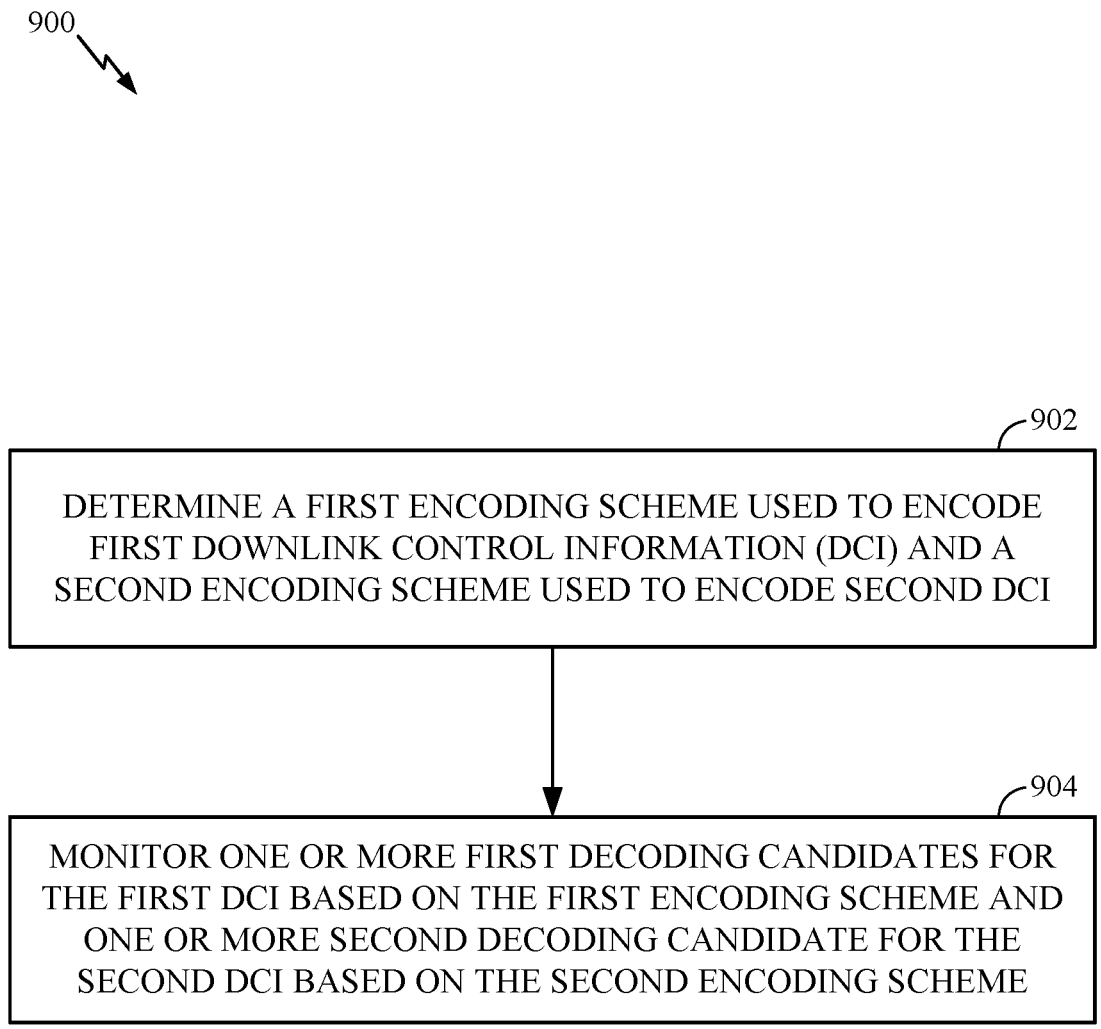
FIG. 9 is a block diagram illustrating example operations for wireless communication by a user-equipment (UE), according to certain aspects of the present disclosure.

FIG. 9 illustrates example operations 900 for wireless communications, in accordance with certain aspects of the presented disclosure. The operations 900 may be performed, for example, by a UE (e.g., UE 120).

Operations 900 may begin at block 902 by determining a first encoding scheme used to encode first downlink control information (DCI) and a second encoding scheme used to encode second DCI. At block 904, the UE may monitor one or more first decoding candidates for the first DCI based on the first encoding scheme and one or more second decoding candidate for the second DCI based on the second encoding scheme.

Figure 10:
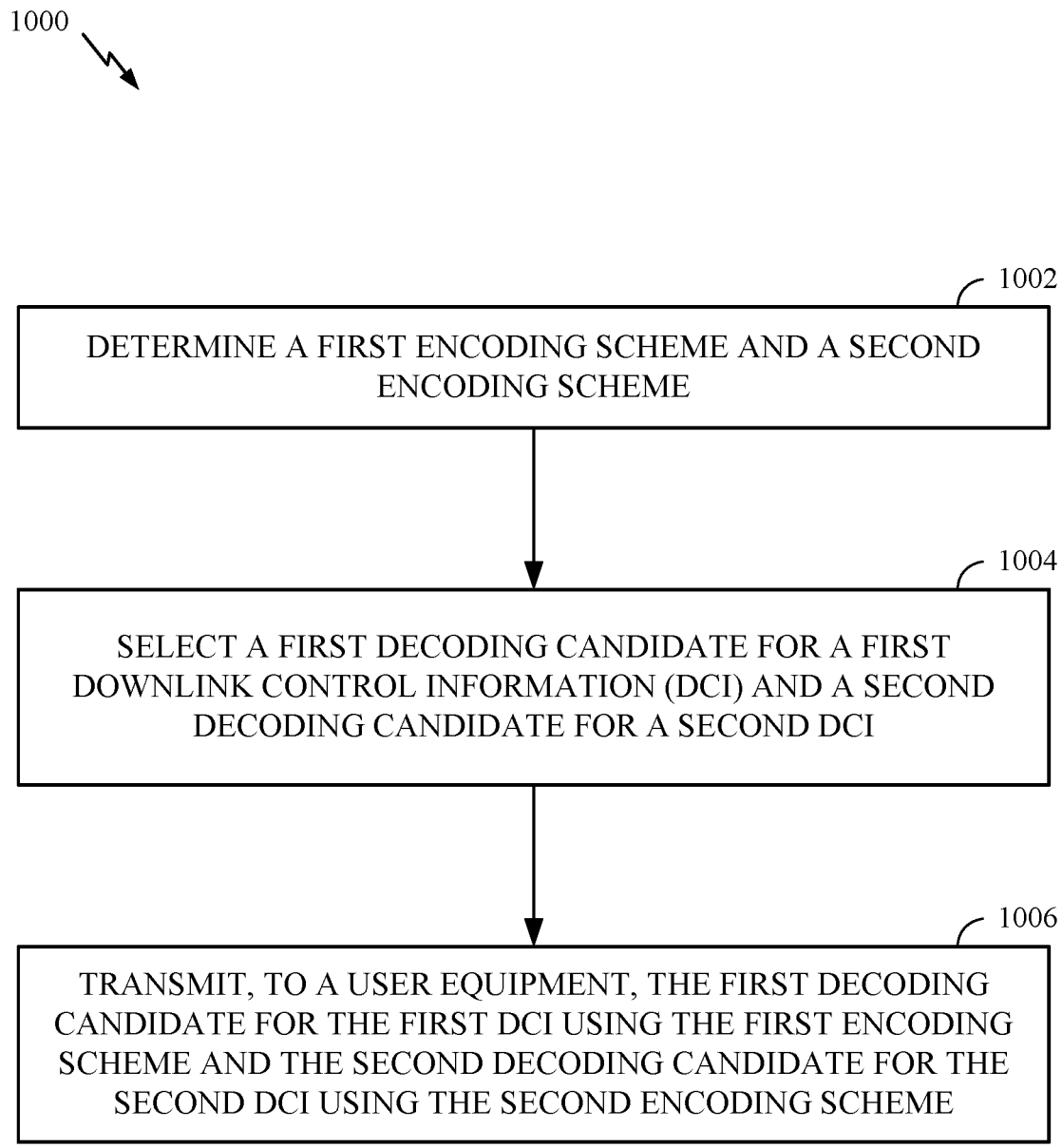
FIG. 10 is a block diagram illustrating example operations for wireless communication by an eNodeB, according to certain aspects of the present disclosure.

FIG. 10 illustrates example operations 1000 for wireless communications, in accordance with certain aspects of the presented disclosure. The operations 1000 may be performed, for example, by an eNodeB (e.g., eNodeB 110).

Operations 1000 may begin at block 1002 by determining a first encoding scheme and a second encoding scheme. At block 1004, the base station may select a first decoding candidate for a first downlink control information (DCI) and a second decoding candidate for a second DCI, and at block 1006, transmit, to a user equipment, the first decoding candidate for the first DCI using the first encoding scheme and the second decoding candidate for the second DCI using the second encoding scheme In certain aspects, the first decoding candidate may be in a CSS and the second decoding candidate may be in a UESS. However, in some aspects, the first and second decoding candidates may be in the same search space, but can be either different decoding candidates or the same decoding candidates. For example, a first decoding candidate having a certain aggregation level (e.g., level 4) may use a first encoding scheme (e.g., TBCC) and the second decoding candidate having the same aggregation level (e.g., level 4) may use a different encoding scheme (e.g., Polar coding).

In certain aspects, the selection of the encoding schemes may be based on a policy or may be explicitly signaled to the UE 120 by the eNodeB 110. For example, in some aspects, based on a policy, decoding candidates in a CSS may be encoded using TBCC, while decoding candidates in UESS may be encoded using TBCC. In certain aspects, the selection of the encoding schemes may be based on at least one of a size or format of the DCI. In some cases, the decoding candidates in UESS may be encoded using TBCC for a first DCI size, but Polar coding for a second DCI size. That is, as presented above, polar coding may not exhibit a noticeable performance gain over TBCC for a certain payload range, e.g., 20-40 bits. Thus, for example, for a DCI size of 20-40 bits, TBCC may be used, and polar coding may be used otherwise. In some cases, a UE configured via higher layers may monitor for a first subset of decoding candidates in UESS assuming TBCC, and a second subset of decoding candidates in UESS with Polar coding.

In certain aspects, the first DCI and the second DCI may be of the same or different sizes and may be of the same or different formats. That is, when using different encoding schemes, even DCIs of the same size can be differentiated without practical ambiguity. For example, the policy used to determine the encoding schemes can be pre-defined or signaled to a UE, as presented above.

In certain aspects, different encoding schemes may be used even though the first decoding candidate is not the same as the second decoding candidate and the first DCI is not the same as the second DCI. For example, in some cases, the first decoding candidate may be different than the second decoding candidate and the first DCI may be the same as the second DCI (e.g., having the same format). In other cases, the first decoding candidate may be the same as the second decoding candidate, but the first DCI may be different than the second DCI.

In some cases, the differentiation of encoding schemes can be linked with radio network temporary identifier (RNTI) types. For example, a DCI associated with SI/P/RA/G/SC/TPC PUCCH/PUSCH RNTI may be encoded using TBCC and a DCI associated with C/SPS-C RNTI can be either TBCC or polar coding.

In certain aspects, the differentiation of encoding schemes can be linked with a duration of the control channel transmission. For example, a control channel without repetition may be encoded based on Polar coding and a control channel with repetition may be encoded based on TBCC.

In certain aspects, the determination of encoding schemes may depend on a capability of the UE (e.g., whether the UE is capable of using URLLC) or the UE category (e.g., type of the UE). For example, decoding candidates transmitted to MTC type UEs may be encoded using TBCC.

In certain aspects, the policy for determination of encoding schemes may be defined on a per component carrier (CC) basis. For example, a first CC may be configured to use TBCC for UESS, while a second CC may be configured to use Polar coding for UESS.

Certain aspects of the present disclosure are directed to a linkage between encoding schemes used for a control channel and a data channel. A DCI associated with an encoding scheme can implicitly carry at least one-bit of information that can be used to determine an encoding scheme used to encode a data channel. That is, there may be an implicit linkage of a coding type between control and data channels. For example, if a control channel is encoded using TBCC, a data channel may be encoded using low-density parity-check (LDPC) or turbo coding. In some cases, if a control channel is encoded using Polar coding, the data channel may be encoded using Polar coding for transport block of a certain payload range, and LDPC or turbo coding for other ranges.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

If implemented in hardware, an example hardware configuration may comprise a processing system in a wireless node. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement the signal processing functions of the PHY layer. In the case of a user terminal 120 (see FIG. 1), a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media including any medium that facilitates transfer of a computer program from one place to another. The processor may be responsible for managing the bus and general processing, including the execution of software modules stored on the machine-readable storage media. A computer-readable storage medium may be coupled to a processor such that the processor can read information from, and write information to, the storage medium. In the alternative, the storage medium may be integral to the processor. By way of example, the machine-readable media may include a transmission line, a carrier wave modulated by data, and/or a computer readable storage medium with instructions stored thereon separate from the wireless node, all of which may be accessed by the processor through the bus interface. Alternatively, or in addition, the machine-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module below, it will be understood that such functionality is implemented by the processor when executing instructions from that software module.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A method for wireless communication, comprising:
   determining a first encoding scheme used to encode first downlink control information (DCI) of a control channel and a second encoding scheme used to encode second DCI of the control channel, wherein the determination of the first encoding scheme or the second encoding scheme is based on a component carrier (CC) used to transmit the first DCI or the second DCI, respectively, and wherein the determination of the first encoding scheme comprises determining the first encoding scheme comprises a tail-biting convolutional code (TBCC) encoding scheme based on the control channel used to transmit the first DCI using channel repetition, wherein the first encoding scheme and the second encoding scheme are different; and
   monitoring one or more first decoding candidates for the first DCI based on the first encoding scheme and one or more second decoding candidates for the second DCI based on the second encoding scheme.

2. The method of claim 1, wherein the determination is further based on a type of search space corresponding to the one or more first decoding candidates or the one or more second decoding candidates.

3. The method of claim 2, wherein the type of search space comprises a user-equipment specific search space (DESS) or a common search space (CSS).

4. The method of claim 2, wherein the type of search space comprises a search space for a first type of service or a search space for a second type of service.

5. The method of claim 1, wherein the determination is further based on a size or format of the first DCI or the second DCI, or a combination of the size and the format.

6. The method of claim 1, wherein the determination is further based on a type of radio network temporary identifier (RNTI) associated with the first DCI or the second DCI.

7. The method of claim 6, wherein the determination is further based on whether the type of RNTI is user-equipment (UE) specific.

8. The method of claim 1, wherein the determination is further based on a duration of the control channel used to transmit the first DCI or the second DCI.

9. The method of claim 1, further comprising:
  determining a third encoding scheme based on the determination of the first encoding scheme or the second encoding scheme; and
  decoding a data channel based on the third encoding scheme.

10. The method of claim 9, wherein determining the third encoding scheme is further based on a payload range of the data channel.

11. The method of claim 1, wherein the first encoding scheme comprises the TBCC encoding scheme and the second encoding scheme comprises polar coding.

12. The method of claim 1, further comprising receiving an indication of a policy for determining an encoding scheme, wherein the determination is based on the indication.

13. The method of claim 1, wherein the method is performed by a user equipment (UE), and wherein the determination is based on a capability or a category of the UE.

14. A method for wireless communication, comprising:
  determining a first encoding scheme and a second encoding scheme, wherein the first encoding scheme and the second encoding scheme are different;
  selecting a first decoding candidate for a first DCI of a control channel and a second decoding candidate for a second DCI of the control channel, wherein the determination of the first encoding scheme or the second encoding scheme is based on a component carrier (CC) used to transmit the first DCI or the second DCI, respectively, and wherein the determination of the first encoding scheme comprises determining the first encoding scheme comprises a tail-biting convolutional code (TBCC) encoding scheme based on the control channel used to transmit the first DCI using channel repetition; and
  transmitting, to a user equipment (UE), the first decoding candidate for the first DCI using the first encoding scheme and the second decoding candidate for the second DCI using the second encoding scheme.

15. The method of claim 14, wherein the determination is further based on a type of search space corresponding to the first decoding candidate or the second decoding candidate.

16. The method of claim 14, wherein the determination is further based on a size or a format of the first DCI or the second DCI, or a combination of the size and the format.

17. The method of claim 14, wherein the determination is further based on a type of radio network temporary identifier (RNTI) associated with the first DCI or the second DCI.

18. The method of claim 14, wherein the determination is further based on a duration of the control channel used to transmit the first DCI or the second DCI.

19. The method of claim 14, further comprising:
  determining a third encoding scheme based on the determination of the first encoding scheme or the second encoding scheme; and
  transmitting a data channel based on the third encoding scheme.

20. The method of claim 19, wherein determining the third encoding scheme is further based on a payload range of the data channel.

21. The method of claim 14, wherein the first encoding scheme comprises the TBCC encoding scheme and the second encoding scheme comprises polar coding.

22. The method of claim 14, wherein the determination is further based on a capability or a category of the UE.

23. The method of claim 14, wherein the determination is further based on a policy, the method further comprising transmitting an indication of the policy to the UE.

24. An apparatus for wireless communication, comprising:
  means for determining a first encoding scheme used to encode first downlink control information (DCI) of a control channel and a second encoding scheme used to encode second DCI of the control channel, wherein the means for determining makes the determination of the first encoding scheme or the second encoding scheme based on a component carrier (CC) used to transmit the first DCI or the second DCI, respectively, and wherein the means for determining determines the first encoding scheme comprises a tail-biting convolutional code (TBCC) encoding scheme based on the control channel used to transmit the first DCI using channel repetition, wherein the first encoding scheme and the second encoding scheme are different; and
  means for monitoring one or more first decoding candidates for the first DCI based on the first encoding scheme and one or more second decoding candidates for the second DCI based on the second encoding scheme.

25. An apparatus for wireless communication, comprising:
  means for determining a first encoding scheme and a second encoding scheme, wherein the first encoding scheme and the second encoding scheme are different;
  means for selecting a first decoding candidate for a first DCI of a control channel and a second decoding candidate for a second DCI of the control channel, wherein the means for determining makes the determination of the first encoding scheme or the second encoding scheme based on a component carrier (CC) used to transmit the first DCI or the second DCI, respectively, and wherein means for determining determines the first encoding scheme comprises a tail-biting convolutional code (TBCC) encoding scheme based on the control channel used to transmit the first DCI using channel repetition; and
  means for transmitting, to a user equipment (UE), the first decoding candidate for the first DCI using the first encoding scheme and the second decoding candidate for the second DCI using the second encoding scheme.

* * * * *